United States Patent [19]
Batchelder et al.

[11] Patent Number: 5,493,515
[45] Date of Patent: Feb. 20, 1996

[54] TWICE SCALED WAVEFORM DISPLAY

[75] Inventors: Paul B. Batchelder, Golden; Jeffrey M. Waynik, Nederland, both of Colo.

[73] Assignee: Ohmeda Inc., Liberty Corner, N.J.

[21] Appl. No.: 309,227

[22] Filed: Sep. 20, 1994

[51] Int. Cl.$^6$ .................................................. G01R 1/08
[52] U.S. Cl. ........................ 364/550; 364/481; 324/115; 345/127
[58] Field of Search ............................ 364/550, 481–487; 395/102, 139, 155; 324/76, 19, 121 R, 115; 345/112–120, 127–130

[56] References Cited

U.S. PATENT DOCUMENTS

| | | | |
|---|---|---|---|
| 4,415,891 | 11/1983 | Hay, III | 345/204 |
| 4,675,147 | 6/1987 | Schaefer et al. | 376/245 |
| 4,864,512 | 9/1989 | Coulson et al. | 364/481 |
| 5,072,168 | 12/1991 | Ferguson | 324/121 R |
| 5,155,431 | 10/1992 | Holcomb | 324/121 R |

*Primary Examiner*—James P. Trammell
*Attorney, Agent, or Firm*—Roger M. Rathbun; Larry R. Cassett; James M. Graziano

[57] ABSTRACT

The twice scaled waveform display apparatus combines a twice scaled factor indication with the autoscaled waveform display so that an input data quality indication is produced based on factors such as signal strength, wherein the twice scaled factor is used to modulate the size of the display that is presented to the user. Thus, the generated waveform occupies a predetermined portion of the display when the signal strength and/or other input data qualities are at an acceptable level. The size of the waveform presented to the user on the display is reduced in magnitude when there is a degradation in the input signal magnitude or other quality factors.

16 Claims, 3 Drawing Sheets

RAW DATA

AUTO SCALED VALUE

TWICE SCALED VALUE

TWICE SCALED WAVEFORM DISPLAY

FIELD OF THE INVENTION

This invention relates to monitoring apparatus and, in particular, to apparatus that provides a compact display which concurrently illustrates several pieces of information to the user in a convenient comprehensible form.

PROBLEM

It is a problem in the field of monitoring systems to produce a display that conveys the maximum amount of information to the user in a compact, yet comprehensible form. Many monitoring systems of necessity must concurrently display the values of a number of different variables to the user. This is generally accomplished by providing a separate display for each of the variables. A difficulty with such an arrangement is that the user must view numerous displays to ascertain the set of information that is of interest to the user. To simplify the displays that present data to the user, many prior art systems simply use a predetermined threshold alert for those variables that are of lesser importance. Thus, a variable, such as input signal strength, is not displayed to the user and an audible alarm is provided only when the input signal strength drops below a predetermined allowable value. The problem with this alternative to the use of complex displays is that the user is provided with no advanced warning of the imminent failure of the system to acquire a sufficient input signal to accurately produce the required display. The user is suddenly presented with an audible alarm indicative of inadequate input signal strength, at which point the validity of the data that is being displayed is called into question and the user has no time to proactively address the input signal strength degradation problem that has been insidiously encroaching on the monitoring process.

Thus, there presently does not exist a good solution to the problem of concurrently displaying the values of multiple variables to a user without adding undue complexity to the display by providing additional display elements to view and interpret, such as indicating the value of a monitored parameter as well as indicating its signal strength to the user on two separate display elements.

SOLUTION

The above-described problems are solved and a technical advance achieved in the field by the twice scaled waveform display apparatus of the present invention. This apparatus produces a unified display that concurrently shows a number of parameters in a simple form so that the user is conveyed the maximum amount of information with a simple display format. This is accomplished by first autoscaling the input data so that a waveform produced on the two-dimensional display to illustrate the magnitude and characteristics of the input data occupies a predetermined portion of the display screen. This technique presents the input data to the user in the maximum size format possible to permit the user to obtain fine detail from the display without having to manually select the range of values that is to be displayed by the apparatus. The twice scaled waveform display apparatus then combines a twice scaled factor indication with the autoscaled waveform display so that an input data quality indication is produced based on factors or characteristics of the input signal, such as signal strength, wherein the twice scaled factor is used to modulate the size of the display that is presented to the user. Thus, the generated waveform occupies a predetermined portion of the display when the input signal strength and/or other input signal qualities are at an acceptable level. The size of the waveform presented to the user on the display is reduced/expanded in magnitude when there is a significant change, such as a degradation, in the input signal magnitude or other quality factors.

The user is therefore alerted to any variation in the magnitude or quality of the input data by a variation in the size of the waveform displayed to the user so that the user can be aware of potential problems with the quality and/or quantity of input data being received by the monitoring apparatus. This enables the user to take remedial action before the input signal becomes of such inferior quality that the monitoring apparatus generates erroneous data or is unable to produce a monitoring output. Thus, the twice scaled waveform display concurrently provides two sets of information to the user in a single form that is easily comprehended by the user and is also simple to generate by the apparatus.

DETAILED DESCRIPTION

Figure 1:
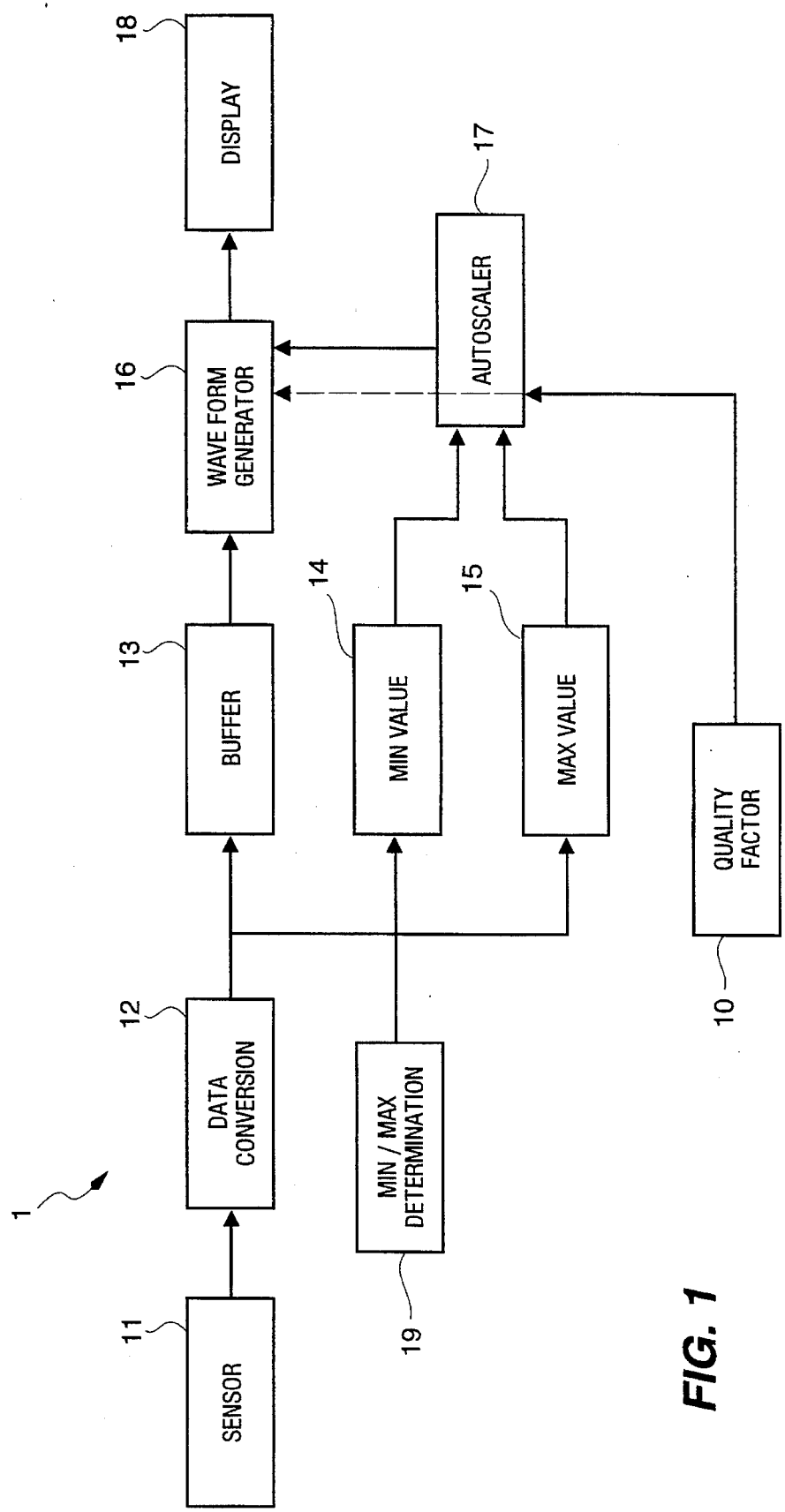
FIG. 1 illustrates in block diagram form the overall architecture of the twice scaled waveform display apparatus of the present invention.
Figure 2:
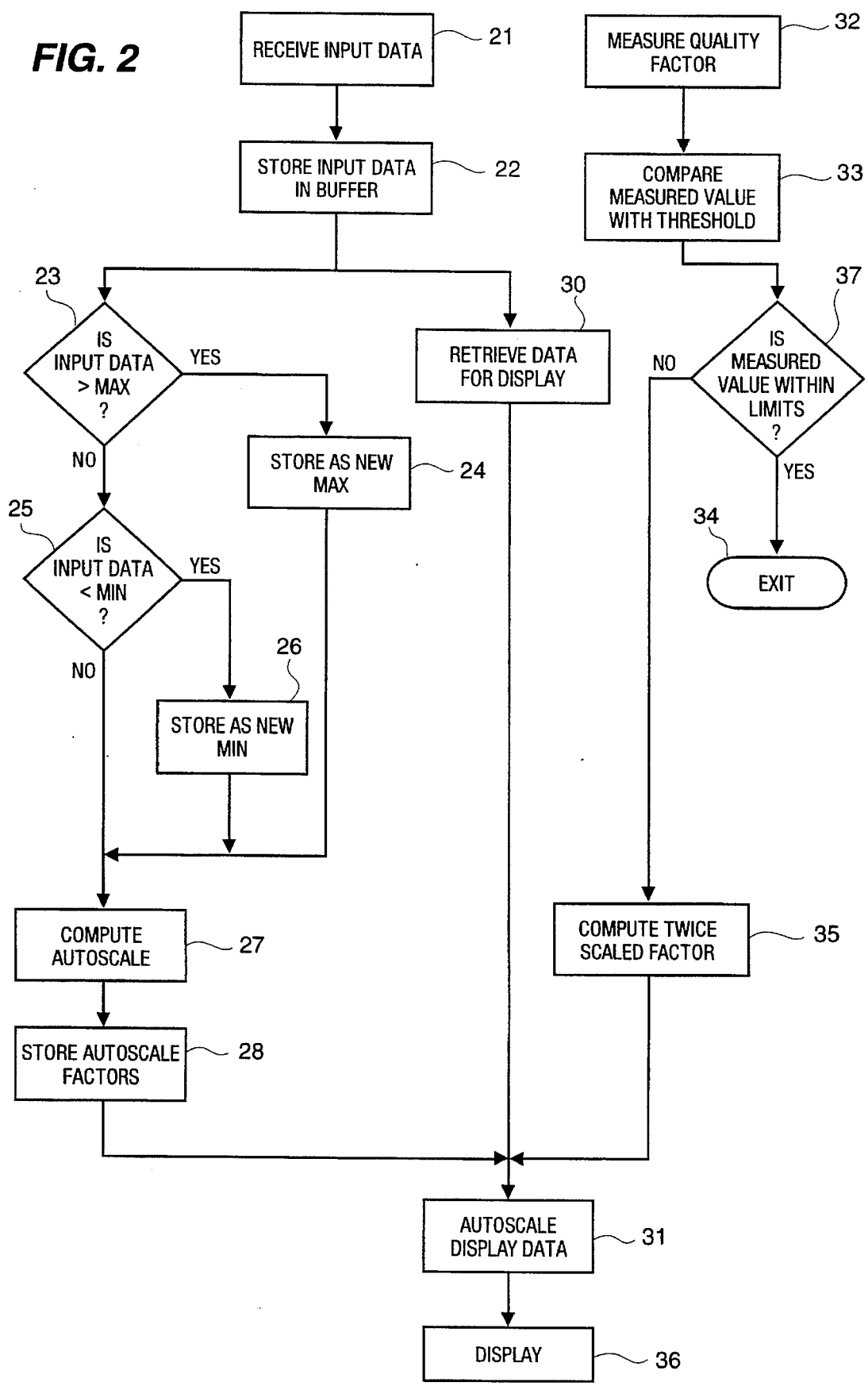
FIG. 2 illustrates in flow diagram form the operational steps taken by the twice scaled waveform display apparatus of the present invention.

FIG. 1 illustrates in block diagram form the twice scaled waveform display apparatus of the present invention and FIG. 2 illustrates in flow diagram form the operation of the twice scaled waveform display apparatus of the present invention. This apparatus is typically used in a monitoring device 1 wherein a sensor 11 affixed to the monitoring device 1 is used to collect input data indicative of some measurable variable. In a medical monitoring environment, the monitoring device 1 typically includes a sensor 11 that is affixed to a patient to measure one or more physiological characteristics of the patient, which characteristics are then displayed to the user in numerical form or as a waveform on a display 18. Such a monitoring device 1 can be an electrocardiogram or a pulse oximeter system wherein the waveform display is indicative of the temporal variation of the monitored physiological characteristic of the patient and presents a significant quantity of information to the user in addition to simple magnitude data.

In a medical monitoring environment, it is not uncommon for the sensor to become loose on patient or to be inaccurately applied to the patient. This improper application of the sensor 11 results in inadequate input signal strength which causes invalid or erratic data to be input to the monitoring device 1. The failure to properly attach the sensor 11 to the patient is not easily detected by the user and most medical monitoring device 1 includes a signal strength bar display that provides the user with an indication of the magnitude of the input signal that is being received from the sensor 11. The difficulty with this arrangement is that the bar display represents yet one more display that the user must view and one more piece of information that the user must integrate in performing their analysis. In many medical monitoring situations, a plurality of monitoring devices are mounted in a rack system so that it may be difficult for the user to maintain the correspondence between the waveform that is being viewed and the corresponding signal strength bar, since the user typically focuses on the waveform as the prime source of information regarding the monitored characteristic. Alternatively, the signal strength bar can be replaced by an audible alarm which indicates when the input signal strength drops below a predetermined threshold.

Figure 3:
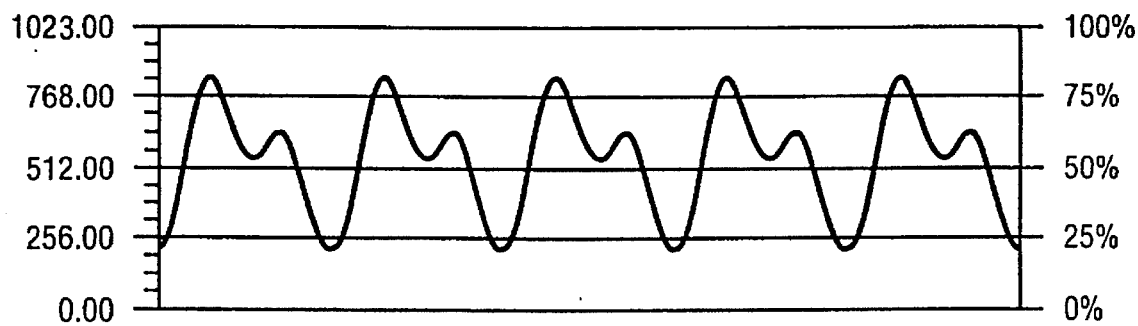
FIGS. 3–5 illustrate displays indicative of the operation of the twice scaled waveform display apparatus of the present invention.
Figure 4:
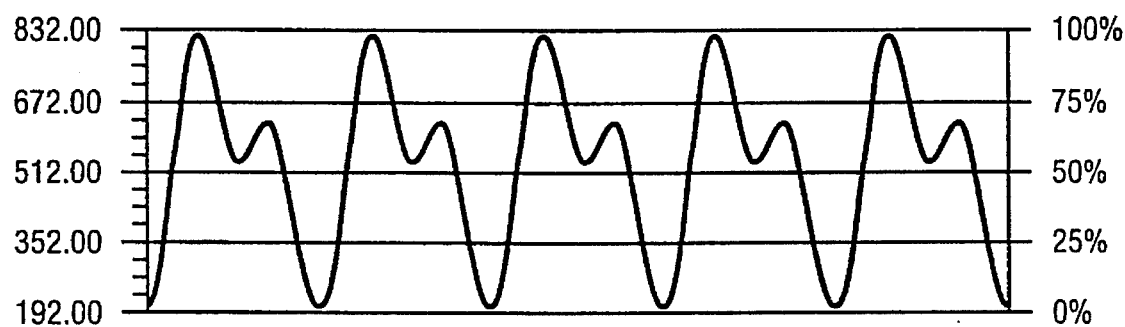
Figure 5:
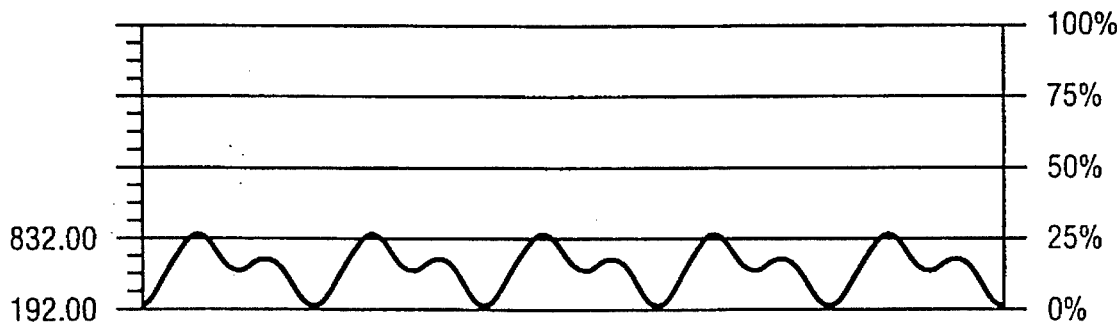

The concurrent display of the monitored characteristic and data indicative of the input signal quality is accomplished by the twice scaled waveform display apparatus which integrates the two sets of information into a unified display output format. In this apparatus, measurement data is received from a signal source, such as a sensor 11 attached to a patient to collect data regarding a physiological characteristic to be measured. The monitoring apparatus 1 converts the signal produced by the sensor 11 to a human readable display that indicates the parameter that is measured. A sequence of measurements is typically made on a periodic basis, and this timewise sequence of samples can be displayed as a waveform on a two-dimensional display element 18. FIGS. 3–5 illustrate typical displays that are produced by monitoring device 1.

In order to produce the resultant waveform display, the input data is periodically sampled and processed by the data converter 12 of the monitoring device 1, and then stored in a buffer memory 13 so that a predetermined number of sampled data values can be recorded for display on the two-dimensional display 18. In addition, maximum data value buffer 15 and minimum data value buffer 14 are provided to store data values indicative of the maximum data value and minimum value that have been encountered over either a predetermined time interval or during this data collection session. Autoscaler 17, in well-known fashion, then uses the maximum and minimum data values that are stored in maximum value buffer 15 and minimum value buffer 14 to compute a scale factor which is used by waveform generator 16 to reduce/expend the size of the waveform display produced on display 18.

FIG. 3 illustrates the waveform that can be produced as a result of collecting the raw input data from the monitoring device 1 and displaying, in a waveform format, a timewise sequence of the sampled data values that are generated. As can be seen from this waveform display, the waveform that is produced is a periodic function having a certain characteristic shape and fairly consistent amplitude swings. The raw data waveform oscillates about a data value of 5 12 as indicated on the lefthand scale and ranges between values of 198 and 832 as also measured on the lefthand scale. The units displayed on this scale are a function of the physiological characteristic being measured, and the values used herein are simply for the purpose of illustrating the concept of the invention. Instead of using the actual measurement scale shown on the left side of FIG. 3, the data of the waveform display 18 can be presented as an indication of a percentage of full scale, such as that illustrated in the righthand side of the display wherein a percentage figure is illustrated to indicate the magnitude of the received value as a percentage of the potential maximum value. As can be seen from this display of FIG. 3, the waveform occupies only 50% of the display area and, while illustrative of the changes taking place in the measured parameter, lacks the fine detail of the changes that in many cases is desirable. Therefore, many monitoring devices autoscale the raw data so that the waveform that is displayed to the user occupies the maximum available physical display space. An example of this autoscaled waveform is illustrated in FIG. 4 wherein the scale on the lefthand side of the display 18 indicates the new (autoscaled) range of measurement values that are being displayed from the minimum value of 198 to the maximum value of 832. Again, since the waveform oscillates around the 512 (median) value, that indicia has not changed on the display 18, but the intermediate values between this median value and the maximum and minimum values are now indicated as 358 and 672. It is obvious that the waveform illustrated in FIG. 4 provides the user with far more detail regarding the subtle changes and specific points on the waveform than the raw data waveform display of FIG. 3. Again, if the waveform is displayed as a percentage value, the scale on the righthand side of the display 18 does not change since this indicates a simple percent of full-scale indication.

Autoscale Function

The autoscale value is typically computed by scaling the range of displayed data values by the presently occurring signal value that is to be displayed. Therefore, the magnitude of the input value that represents full-scale is computed by dividing the value required to achieve a full-scale data point on the display device by the range of expected or occurring data values represented by the maximum data value minus the minimum data value in the presently occurring data collection. (This can also be an historic range of minimum and maximum values.) As shown in FIG. 2, at step 21 input data is received from data converter 12 and stored at step 22 in buffer memory 13. At step 23, the minimum/maximum value determining circuit 19 compares the received input data value to the data value stored in maximum value buffer memory 15 and, if the received input data value is a new maximum, it is stored in maximum value buffer memory 15 at step 24 and processing advances to step 27.

If the received input data value is not greater than the presently stored maximum value, minimum/maximum value determining circuit 19 at step 25 compares the received input data value with the minimum data value stored in the minimum value buffer memory 14. If the received input data value is less than the presently stored minimum data value, the input data value is a new minimum and the minimum/maximum value determining circuit 19 at step 26 stores this input data value in minimum value buffer memory 14 and processing advances to step 27. If the presently received input data value is not less than the presently stored minimum data value, processing advances to step 27. At step 27, autoscaler 17 computes the display scale and stores, at step 28, these computed autoscale values in a memory, which can be located in waveform generator 16. These stored autoscale values serve to recalibrate the display parameters and are used to map the raw data of FIG. 3 to produce the autoscaled display of FIG. 4. The waveform display is produced by waveform generator 16 at step 30 reading a set of data values from buffer memory 13, which set of data values is used to generate the waveform display that illustrates the time-varying monitored characteristics. The retrieved set of data values is then autoscaled prior to being transmitted to display 18. This is accomplished at step 31 by multiplying the revised full-scale definition of display 18 by the difference between the presently obtained raw input data value and the stored minimum data value. The resultant number can then be used by the display device 18 to display the data point which would occur at a point between the minimum data value and the maximum data value. Since the minimum and maximum data value used to create the revised fullscale display are the data values collected over this data collection period or historic maximum and minimum values, it is unlikely that the raw data that is received by this apparatus will exceed the limits that are established using this procedure. However, if a new minimum or maximum data value occurs, the full-scale display limits are revised by this apparatus to present a new range of values that can be displayed on the display 18. In performing the autoscale function, it is standard practice to filter the input signal and perform whatever smoothing functions are required to clean up the display to present the information to the user in the most understandable form.

Twice Scaled Display

A difficulty with displaying an autoscaled value is that the input signal on which all of the measurements are based can be degraded in magnitude or quality to a point where it is imminently unusable. This situation is not conveyed to the user by the autoscaled display. Therefore, the apparatus of the twice scaled waveform display modulates the autoscaled display by a twice scaled factor which is the result of multiplying the autoscaled value computed above by the ratio of a presently determined quality factor divided by a maximum possible quality factor. The process is initiated at step 32 where quality factor circuit 10 measures a quality factor. A quality factor can be any typical parameter or characteristic of the input signal, such as input signal strength or percent modulation or any other indicator of the quality and reliability of the input signal. At step 33, quality factor circuit 10 compares the measured quality factor with a predetermined quality factor value indicative of a desired value of this factor. If the measured quality factor value exceeds the predetermined quality factor value, processing exits at step 34 and the twice scaled factor is 1, indicating full scale display. If the measured quality factor value is less than the predetermined desired quality factor value, quality factor circuit 10 at step 35 computes a new twice scaled factor that is used to reduce (or expand) the magnitude of the waveform displayed on display device 18. The twice scaled factor produced by quality factor circuit 10 is typically the ratio of the presently measured value of the quality factor divided by the predetermined quality factor value indicative of a desired value for this factor. This ratio indicates the amount that the generated autoscaled waveform should be reduced to indicate a reduction in the quality of the input signal. The simple ratio computation is but one of the many algorithms that can be used to compute a twice scaled factor and is noted for the purpose of illustrating the twice scaled factor concept and is not intended to limit the twice scaled factor computation. Thus, the input signal has a number of characteristics, one of which represents a value of the monitored variable. One or more of the remaining input signal characteristics (quality factor) can then be used to determine the "quality" of the input signal to produce an indication (twice scaled factor) to the user of the integrity of the input signal that is presently being received.

The computed twice scaled factor is output by quality factor circuit 10 to waveform generator 16 which uses the twice scaled factor to modulate the size of the autoscaled waveform. Alternatively, the twice scaled factor can be transmitted to autoscaler 17 which automatically adjusts the display parameters. Therefore, the display of FIG. 5 indicates the autoscaled value as modulated by the twice scaled factor to represent the raw data as in the previous autoscaled display but with the maximum magnitude of the signal being an indication of the quality of the raw data that is being received. Therefore, if the input signal strength is significantly degraded, the waveform display of FIG. 5 indicates to the user that the received data is based on an input signal that is of marginal magnitude/quality. The scale values displayed on the lefthand side of the display 18 again represent the measured value which ranges between 198 and 832 as in the autoscaled display; however, the waveform occupies only ¼ of the display screen thereby indicating the input signal strength or other quality factor that is used to perform the measurement is only ¼ of the desired value. This display provides the user with an indication of a potential problem with the input data that is being received and enables the user to take remedial action before the input signal quality is reduced to the point where the monitoring apparatus canot produce valid data.

Using the system described above, as an example consider a monitoring system that measures a parameter that can vary in value from 0 to 1023. The display of FIG. 3 illustrates the raw data and the fact that the raw data can vary from a minimum value of 0 to a maximum value of 1023. To autoscale this waveform, the formula noted above for autoscaling must be used to determine the value to be displayed on the display 18. The full scale of the display is 1023, and this number must be divided by the difference between the maximum and minimum values that have been encountered during this display period. The maximum value is 832 and the minimum value is 198 which results in a difference between maximum and minimum values of 634. In addition, the difference between the present value and the minimum value must be computed and, assuming a present value of 559, this difference results in a value of 361. Using the formula noted above which alters the present value by the ratio of maximum to minimum values, the present value to be displayed is 583. To twice scale this value, the autoscaled value must be factored by the twice scaled factor. Assume for the purpose of example that the present signal strength is 8 out of a possible 32. This results in a twice scaled factor of ¼ which reduces the displayed value to 145.75. This value would then be displayed as indicated in FIG. 5 to illustrate the modification of the autoscaled value to present the user with an indication of signal strength concurrently on the single display.

We claim:

1. Apparatus for concurrently displaying a plurality of information on a single display comprising:

means for storing a plurality of data values, said plurality of data values being indicative of a sequence of measurements of a monitored variable;

means for autoscaling said plurality of data values to produce a display on a display device indicative of said plurality of data values;

means for determining a characteristic of said measurements;

means for computing a twice scaled factor based on said determined characteristic; and means for modulating a magnitude of said display as a function of said computed twice scaled factor.

2. The apparatus of claim 1 wherein each of said sequence of measurements is taken on an input signal that has a plurality of characteristics, at least one of which is indicative of a value of said monitored variable.

3. The apparatus of claim 2 wherein:

said determining means measures a characteristic of said input signal other than said value of said monitored variable; and said computing means comprises:

means for comparing said measured input signal characteristic with a predetermined threshold;

means for producing a twice scaled factor value that is indicative of a magnitude of a difference between said measured input signal characteristic and said predetermined threshold.

4. The apparatus of claim 3 wherein said modulating means comprises:

means for adjusting a magnitude of said display proportional to said twice scaled factor value.

5. A method for concurrently displaying a plurality of data on a single display comprising the steps of:

storing a plurality of data values, said plurality of data values being indicative of a sequence of measurements of a monitored variable;

autoscaling said plurality of data values to produce a display on a display device indicative of said plurality of data values;

determining a characteristic of said measurements;

computing a twice scaled factor based on said determined characteristic; and modulating a magnitude of said display as a function of said computed twice scaled factor.

6. The method of claim 5 wherein each of said sequence of measurements is taken on an input signal that has a plurality of characteristics, at least one of which is indicative of a value of said monitored variable.

7. The method of claim 6 wherein:

said step of determining measures a characteristic of said input signal other than said value of said monitored variable; and said step of computing comprises:

comparing said measured input signal characteristic with a predetermined threshold;

producing a twice scaled factor value that is indicative of a magnitude of a difference between said measured input signal characteristic and said predetermined threshold.

8. The method of claim 7 wherein said step of modulating comprises:

adjusting a magnitude of said display proportional to said twice scaled factor value.

9. Apparatus for concurrently displaying a plurality of information on a single display comprising:

means for storing a set of data, said set of data comprising a plurality of data values that are time-ordered successively taken measurements of a monitored variable;

means for autoscaling said plurality of data values;

means, using said autoscaled set of data values, for generating a waveform display on a display device, which waveform display is indicative of said plurality of data values;

means for determining a characteristic of said measurements;

means for computing a twice scaled factor based on said determined characteristic; and means for modulating a magnitude of said display as a function of said computed twice scaled factor.

10. The apparatus of claim 9 wherein each of said sequence of measurements is taken on an input signal that has a plurality of characteristics, at least one of which is indicative of a value of said monitored variable.

11. The apparatus of claim 10 wherein:

said determining means measures a magnitude of said input signal; and said computing means comprises:

means for comparing said measured input signal magnitude with a predetermined threshold;

means for producing a twice scaled factor value that is indicative of a magnitude of a difference between said measured input signal magnitude and said predetermined threshold when said measured input signal magnitude is less than said predetermined threshold.

12. The apparatus of claim 11 wherein said modulating means comprises:

means for decreasing a magnitude of said display proportional to said twice scaled factor value.

13. A method for concurrently displaying a plurality of data on a single display comprising the steps of:

storing a set of data, said set of data comprising a plurality of data values that are time-ordered successively taken measurements of a monitored variable;

autoscaling said plurality of data values;

generating, using said autoscaled set of data values, a waveform display on a display device, which waveform display is indicative of said plurality of data values;

determining a characteristic of said measurements;

computing a twice scaled factor based on said determined characteristic; and modulating a magnitude of said display as a function of said computed twice scaled factor.

14. The method of claim 13 wherein each of said sequence of measurements is taken on an input signal that has a plurality of characteristics, at least one of which is indicative of a value of said monitored variable.

15. The method of claim 14 wherein:

said step of determining measures a magnitude of said input signal; and said step of computing comprises:

comparing said measured input signal magnitude with a predetermined threshold;

producing a twice scaled factor value that is indicative of a magnitude of a difference between said measured input signal magnitude and said predetermined threshold when said measured input signal magnitude is less than said predetermined threshold.

16. The method of claim 15 wherein said step of modulating comprises:

decreasing a magnitude of said display proportional to said twice scaled factor value.

* * * * *